US010849773B2

(12) United States Patent
Ryan

(10) Patent No.: US 10,849,773 B2
(45) Date of Patent: Dec. 1, 2020

(54) STENT DELIVERY DEVICE

(71) Applicant: Cook Medical Technologies LLC, Bloomington, IN (US)

(72) Inventor: Michael Ryan, Limerick (IE)

(73) Assignee: Cook Medical Technologies LLC, Bloomington, IN (US)

(*) Notice: Subject to any disclaimer, the term of this patent is extended or adjusted under 35 U.S.C. 154(b) by 735 days.

(21) Appl. No.: 14/537,151

(22) Filed: Nov. 10, 2014

(65) Prior Publication Data
US 2015/0057741 A1  Feb. 26, 2015

(51) Int. Cl.
A61F 2/966 (2013.01)
A61M 16/04 (2006.01)
A61F 2/04 (2013.01)
A61B 90/00 (2016.01)
A61F 2/95 (2013.01)

(52) U.S. Cl.
CPC ......... A61F 2/966 (2013.01); A61M 16/0406 (2014.02); A61B 2090/062 (2016.02); A61F 2/9517 (2020.05); A61F 2002/044 (2013.01); A61F 2250/0097 (2013.01)

(58) Field of Classification Search
CPC ...... A61F 2/966; A61F 2/95; A61F 2002/044; A61F 2250/0097; A61F 2/962; A61M 16/0406; A61B 2090/062
See application file for complete search history.

(56) References Cited

U.S. PATENT DOCUMENTS 5,603,698 A    2/1997  Roberts et al.
5,817,102 A *  10/1998 Johnson ............... A61F 2/07
                                                    606/108
(Continued)

FOREIGN PATENT DOCUMENTS

CA         2179668        11/1993
CN       101516296 A       8/2009
(Continued)

OTHER PUBLICATIONS

International Search Report for corresponding PCT Application No. PCT/US2015/056815, dated Jan. 22, 2016, 4p.
First Office Action and Search Report for related application CN 201580072712.7, dated May 4, 2018, including English Language translation, 15p.
(Continued)

Primary Examiner — Shaun L David
Assistant Examiner — Christina C Lauer
(74) Attorney, Agent, or Firm — Brinks Gilson & Lione

(57) ABSTRACT

A delivery assembly and methods for accurately positioning a stent within a body lumen are disclosed. The delivery assembly comprises a stent releasably attached to the distal end of an inner catheter. A handle at the proximal end of the assembly is operatively connected to the proximal end of an outer catheter and is configured for imparting axial movement to the outer catheter. A sheath is fixed to the handle or inner catheter and disposed about at least a portion of the outer catheter. The sheath comprises indicia visible to the user of the assembly to identify a particular measured distance from a selected point on the sheath to a selected point on one or more components of the delivery device. The inner catheter and sheath are fixed components that do not move relative to each other during axial movement of the outer catheter.

10 Claims, 3 Drawing Sheets

(56) References Cited

U.S. PATENT DOCUMENTS

| | | | |
|---|---|---|---|
| 5,824,041 A * | 10/1998 | Lenker | A61F 2/91 606/195 |
| 5,984,964 A | 11/1999 | Roberts et al. | |
| 6,136,006 A | 10/2000 | Johnson et al. | |
| 6,143,016 A * | 11/2000 | Bleam | A61F 2/958 604/104 |
| 8,048,086 B2 * | 11/2011 | Lee-Sepsick | A61F 6/225 606/108 |
| 8,556,959 B2 | 10/2013 | Goto | |
| 2005/0059990 A1 * | 3/2005 | Ayala | A61B 1/018 606/192 |
| 2005/0149159 A1 * | 7/2005 | Andreas | A61F 2/95 623/1.11 |
| 2005/0273151 A1 * | 12/2005 | Fulkerson | A61F 2/966 623/1.11 |
| 2010/0168834 A1 * | 7/2010 | Ryan | A61F 2/95 623/1.11 |
| 2014/0330362 A1 | 11/2014 | Jimenez, Jr. et al. | |

FOREIGN PATENT DOCUMENTS

| | | |
|---|---|---|
| CN | 202020777 U | 11/2011 |
| EP | 1 815 821 A1 | 8/2007 |
| JP | 1995-502673 A | 3/1995 |
| WO | WO 93/22986 | 11/1993 |
| WO | WO 2010/044856 A1 | 4/2010 |

OTHER PUBLICATIONS

Office Action from corresponding Japanese application 2017-544274, dated Mar. 27, 2019, 3p, in Japanese.

Office Action from corresponding Japanese application 2017-544274, dated Mar. 27, 2019, 2p, English language translation.

Office Action from corresponding Japanese application 2017-544274, dated May 2, 2018, 4p, in Japanese.

Office Action from corresponding Japanese application 2017-544274, dated May 2, 2018, 3p, English language translation.

* cited by examiner

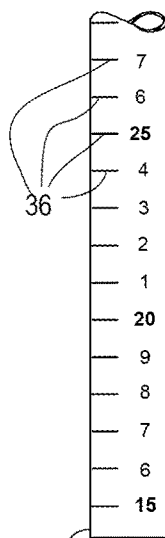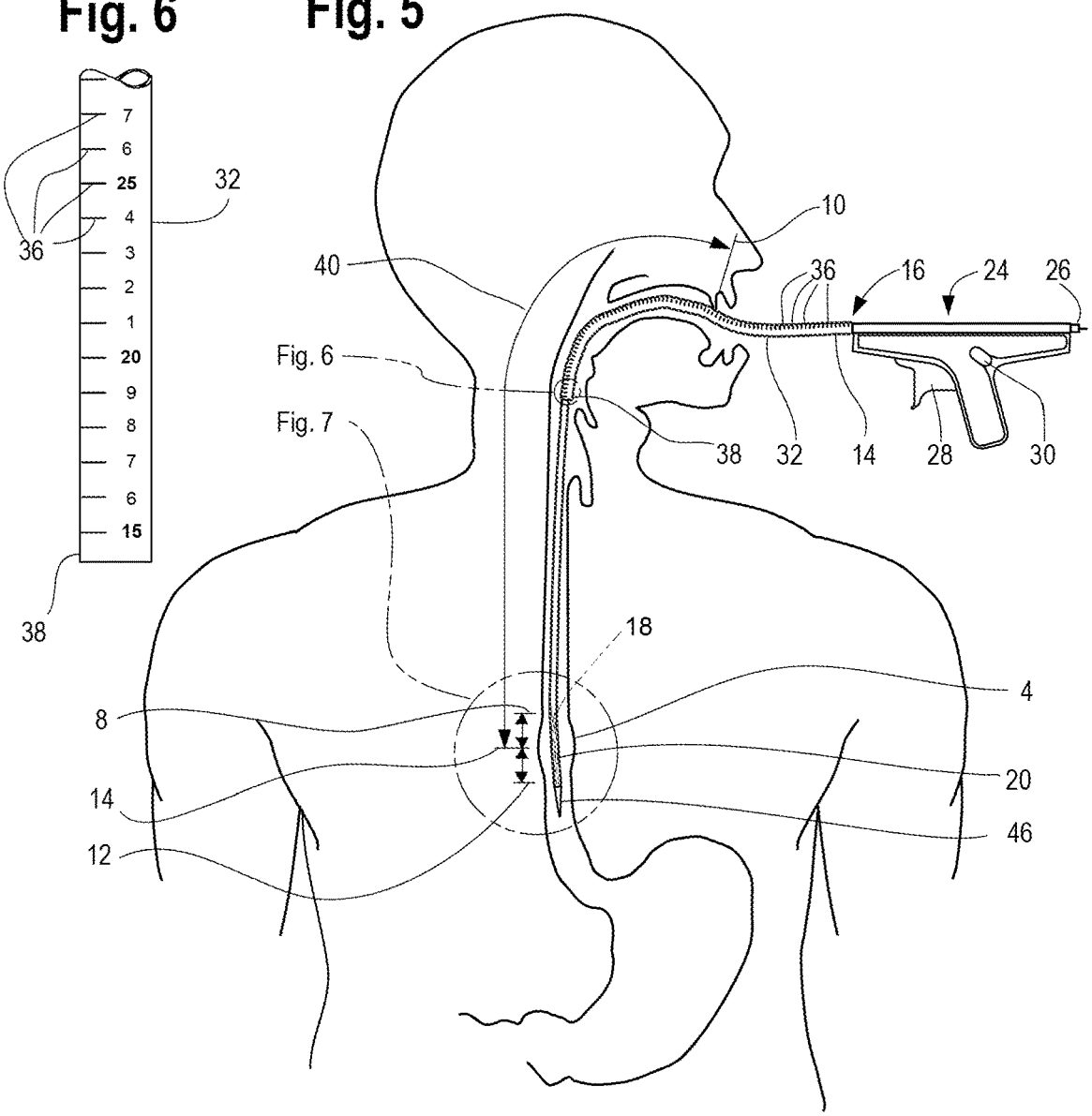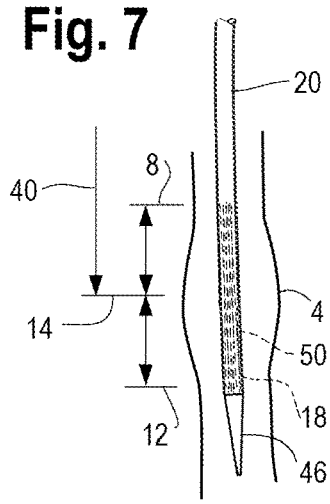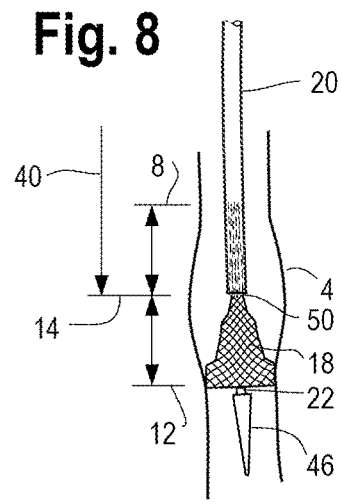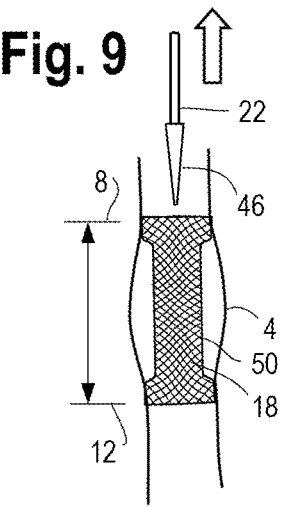

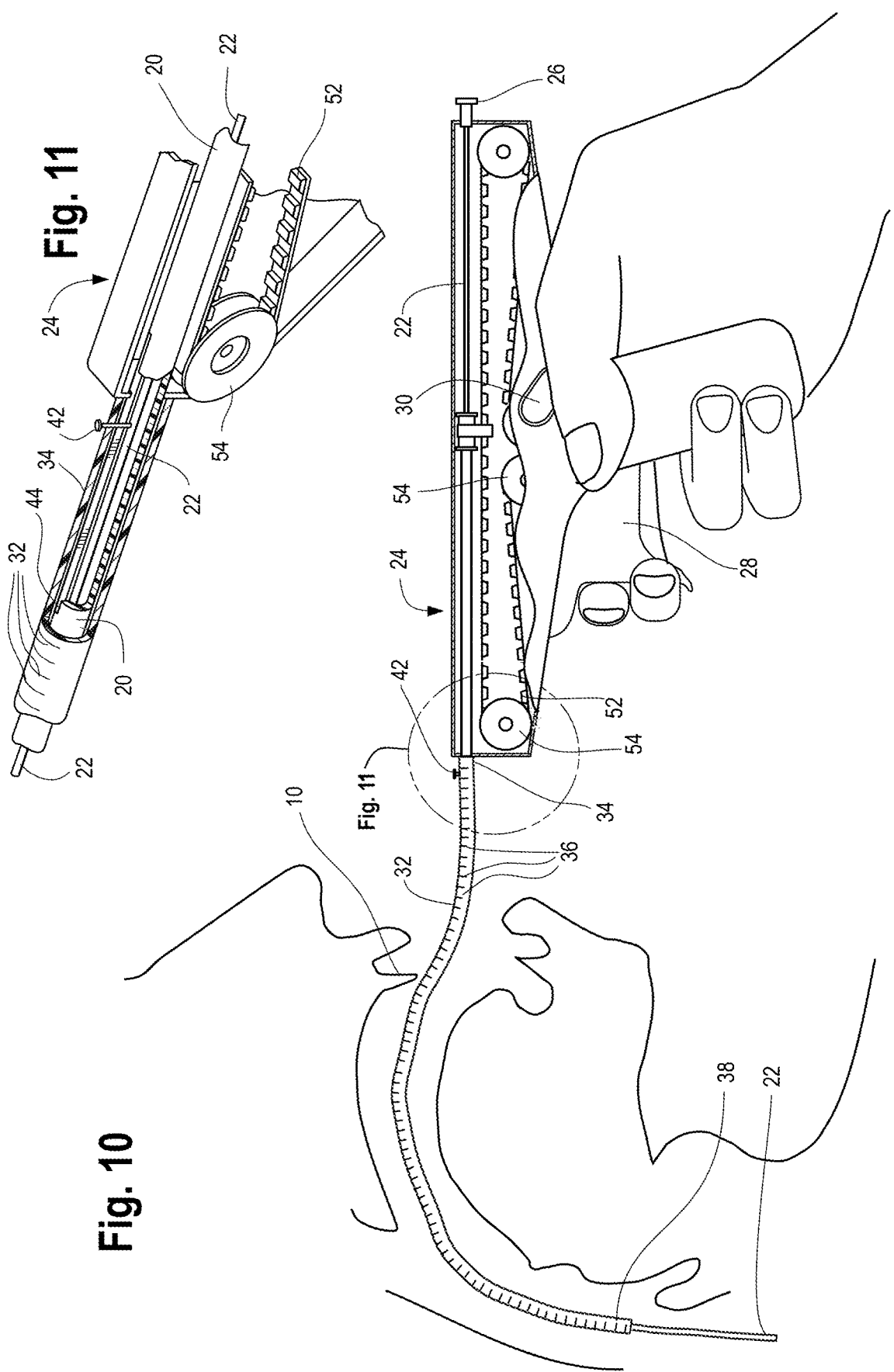

STENT DELIVERY DEVICE

FIELD OF THE INVENTION

The present invention relates to medical devices generally for delivering and deploying a prosthesis in a body lumen or vessel.

BACKGROUND

For patients suffering from a diseased body lumen or vessel, stents are often used to restore functionality and patency to the affected or diseased area. A delivery device with a stent carried on the distal end thereof may be used to deliver the stent to a desired location within a patient's body. A delivery device may include an outer cannula or sheath coaxially disposed and slidable over an inner catheter. The stent is disposed at the distal end of the device between the inner catheter and the outer sheath and is held in a radially inwardly compressed delivery position by the outer sheath. The stent may be deployed by pulling back on the outer sheath to retract it in a proximal direction relative to the inner catheter until the stent is exposed. The stent expands within the body lumen from the stent distal end to the stent proximal end as the sheath is proximally withdrawn.

Accurate positioning of the stent within a body lumen may be visualized by various known methods including endoscopy, fluoroscopy and the like. When using endoscopy, a physician may use an endoscope to determine the location, size and other characteristics of the affected portion of the body. The delivery device may then be used to facilitate accurate delivery of the stent to the particular location of the body as measured and determined by the endoscope.

It is desirable to have a stent delivery device with markings and/or other indicia that provide the physician control over the position and/or orientation of the stent to aid in accurate stent placement and deployment.

SUMMARY

An assembly for delivering an endoluminal prosthesis to a patient is disclosed. In one example, the assembly comprises a proximal end and a distal end and an inner catheter extending between the proximal and distal ends. An endoluminal prosthesis is releasably attached to or disposed about the distal end of the inner catheter. An outer catheter is disposed about at least a portion of the prosthesis. A handle is located at the proximal end of the assembly and is operatively connected to the inner catheter and the outer catheter, and is configured for imparting axial movement to the outer catheter relative to the inner catheter. The outer catheter is moved proximally relative to the inner catheter to expose and deploy the prosthesis. A steady sheath is fixed to the handle and disposed about at least a portion of the outer catheter. The steady sheath comprises indicia visible to the user of the assembly to identify a particular measured distance from a selected point on the steady sheath to a selected point on one or more components of the delivery device. In an exemplary embodiment, the indicia indicates the distance from the midpoint of the prosthesis. The inner catheter, steady sheath and handle are fixed components that do not move relative to each other during axial movement of the outer catheter.

Methods for delivering an endoluminal prosthesis to a patient are also disclosed. In one example, the method comprises determining the location of a lesion within a body lumen and inserting a distal end of a delivery device into the body lumen. The delivery device comprises an inner catheter, an endoluminal prosthesis releasably attached to the distal end of the inner catheter, an outer catheter movably disposed about at least a portion of the prosthesis, a handle at a proximal end of the device, and a steady sheath fixed to the handle and disposed about at least a portion of the outer catheter. The steady sheath comprises indicia visible to the user identifying a particular measured distance from a selected point on the steady sheath to a selected point on the prosthesis. The method further comprises observing the indicia to determine the position of the prosthesis within the body lumen and withdrawing the outer catheter to deploy the prosthesis within the body lumen.

DESCRIPTION OF THE DRAWINGS

FIG. 5 is one example of a stent delivery device inserted into a body lumen for the delivery and deployment of a stent in a desired location.

FIG. 6 is an enlarged view of a portion of the stent delivery device of FIG. 5 having incremental markings or measurements which facilitate accurate positioning and deployment of a stent in a desired location.

FIG. 7 is an enlarged view of the distal end of the delivery device of FIG. 5 delivering a stent to a desired position within a body lumen.

FIG. 8 illustrates withdrawal of an outer catheter to deploy a portion of the stent within a body lumen.

FIG. 9 illustrates a stent fully deployed within a body lumen and withdrawal of the delivery device.

FIG. 10 illustrates a partial cut-away side view of a stent delivery device in use.

FIG. 11 illustrates the proximal end of a steady sheath secured to the distal end of the handle of the delivery device with a pin connecting the steady sheath to the inner catheter.

DETAILED DESCRIPTION

Throughout the specification, the terms "distal" and "distally" shall denote a position, direction, or orientation that is generally away from the physician. The terms "proximal" and "proximally" shall denote a position, direction, or orientation that is generally towards the physician.

A device for delivering and deploying a prosthesis in a body lumen or vessel is described herein. The device may be particularly useful in delivering a prosthesis (e.g., a self-expanding stent) to a patient using one or more technologies such as endoscopy, however, fluoroscopy and other known technologies are also contemplated which aid in the visualization and accurate positioning of a stent in a body lumen.

Figure 1:
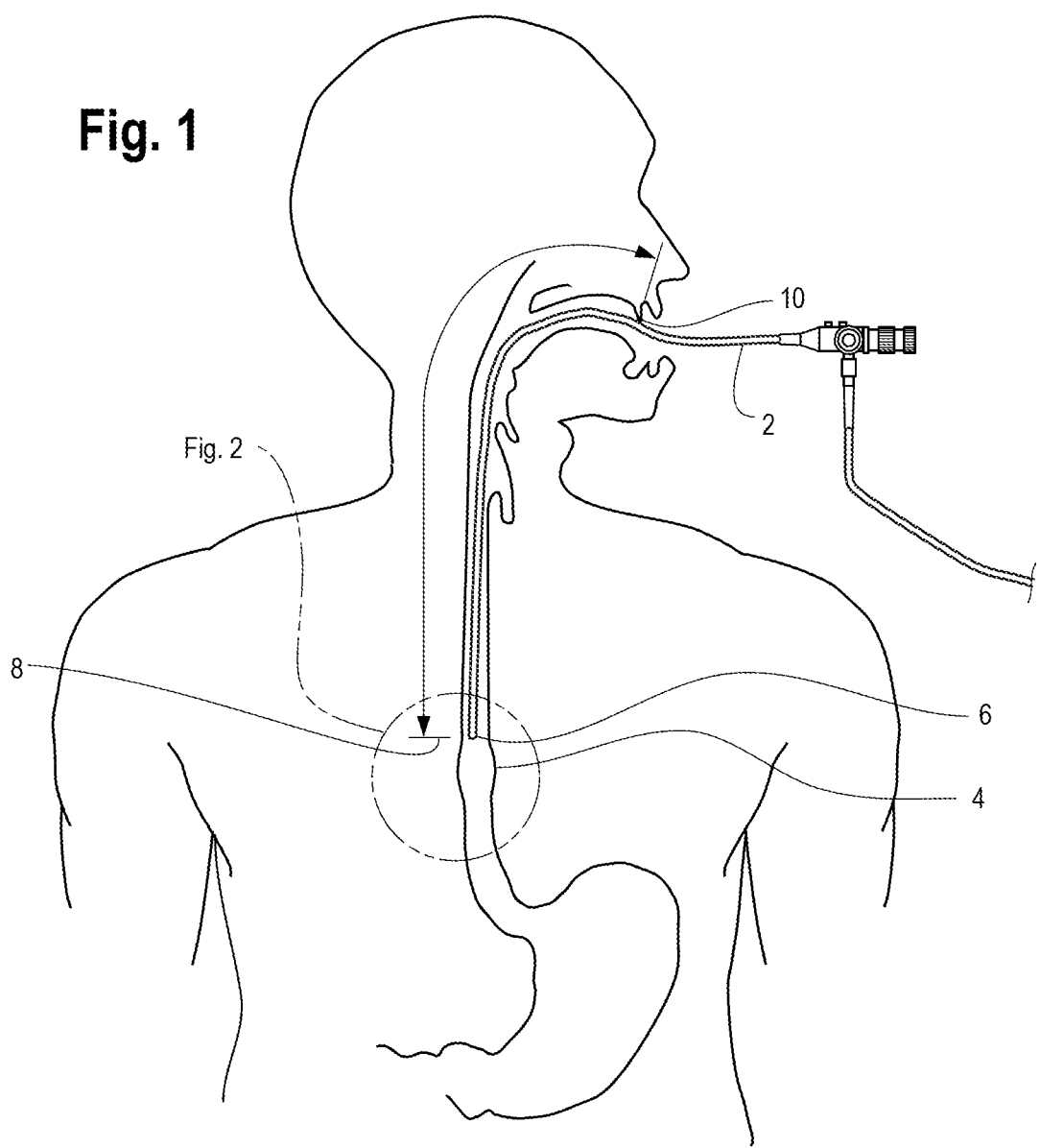
FIG. 1 illustrates an endoscope inserted into a body lumen, such as an esophagus, to locate and evaluate an esophageal lesion.
Figure 2:
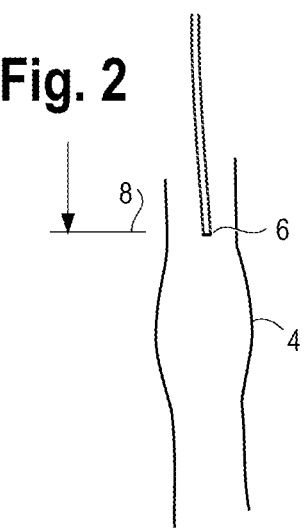
FIG. 2 is an enlarged view of the distal end of the endoscope of FIG. 1 measuring the location of the proximal end of an esophageal lesion.
Figure 3:
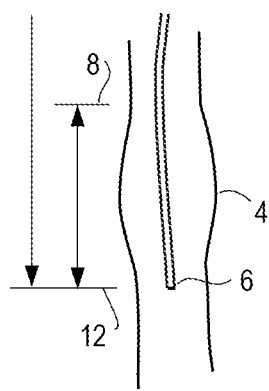
FIG. 3 is an enlarged view of the distal end of the endoscope of FIG. 1 measuring the location of the distal end of an esophageal lesion.
Figure 4:
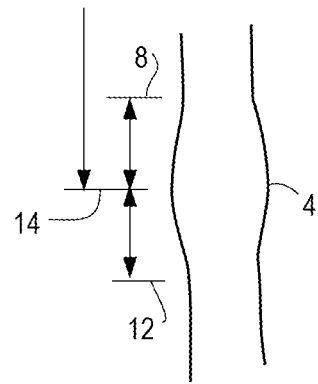
FIG. 4 is an enlarged view of a portion of the esophagus of FIG. 1 identifying a midpoint of an esophageal lesion based on the measurements made with an endoscope in FIGS. 2 and 3.

When using endoscopy to visualize delivery of a stent to a patient, an endoscope 2 may be used to determine the location, size, dimension and other characteristics of a particular lesion 4, wound, diseased or affected area into which placement of a stent or other prosthesis is necessary or desired. FIG. 1 illustrates one example of an endoscope 2 inserted through a patient's mouth and into the esophagus. The distal end 6 of the endoscope 2 may be used to view, assess and measure the lesion 4. Oftentimes, such measurements are taken from a fixed point on the patient's body, such as the patient's teeth 10. As shown in an enlarged view of a portion of the esophagus in FIG. 2, the distal end 6 of the endoscope 2 allows the physician to locate the upper (proximal) most end 8 portion of a lesion 4 as measured from the patient's teeth 10. As the endoscope 2 is extended further into the esophagus, the lower (distal) most end 12 of the lesion 4 can be identified and measured. Obtaining these measurements allows the physician to calculate a middle or center portion 14 of the lesion 4, as illustrated in FIG. 4, where:

a) the length of lesion 4=lower distance 12–upper distance 8: and wherein b) the middle point 14 of a lesion 4=upper distance 8+(lower distance 12–upper distance 8/2).

In addition to taking such measurements, the endoscope 2 may also be used to make other necessary observations, such as to view other portions of the body lumen, investigate the potential existence of other lesions and/or otherwise determine the health status of the patient. Before the endoscope 2 is withdrawn or removed from the body, it may be preferable to insert a guide wire (not shown) through one or more lumens of the endoscope. This allows a delivery device or other instruments to be tracked over the guide wire and into a desired position within the patient, as illustrated and discussed in connection with FIG. 5, after the endoscope 2 has been removed.

FIG. 5 illustrates one example of a stent delivery device 16 for delivering a stent 18 to a body lumen (see FIG. 7). As shown, the stent 18 may be an esophageal stent for the treatment of a variety of benign and malignant esophageal conditions. Benign conditions include refractory strictures (such as those induced by peptic ulcers, anastomoses, and radiation), tracheoesophageal fistulae, iatrogenic perforations, and leaks. Malignant conditions that can be treated with stents include inoperable esophageal cancer, gastroesophageal junction cancer, and gastric cardia cancer. However, the stent delivery device 16 may also be used for the delivery, placement and deployment of a prosthesis in a variety of body lumens or vessels, including, but not limited to a patient's vascular system, gastrointestinal system and other body organs or lumens.

As shown in FIG. 5, one example of a delivery device 16 has been inserted into a patient's mouth and extended distally into the esophagus. A prosthesis, such as a stent 18, is carried on the distal end of the delivery device 16 in a constrained configuration by an outer sheath or catheter 20 (as shown in FIG. 7) and collapsed against an inner catheter 22. The stent 18 may be held in the constrained configuration by the outer catheter 20 alone, or in combination with one or more additional stent retention mechanisms (not shown) that may be provided. Such additional stent retention mechanisms may include, for example a proximal and/or distal stent sutures, loops, lassos, diameter-reducing ties or constraining members (not shown), one example of which is described in U.S. Pat. Publication 2011/0190865, and in particular, to FIGS. 5A-5D, 6A-6H and the accompanying disclosure thereof (Cook Medical Technologies, Bloomington, Ind.), which is incorporated by reference herein in its entirety.

The stent 18 may be any kind of stent that can be radially collapsed when a longitudinal or radial force is applied to the ends or outer surface of the stent. By way of non-limiting example, the stent 18 may be formed from one or more of the following materials: nickel titanium alloys, for example, nitinol, stainless steel, cobalt alloys and titanium alloys, and may also include radiopaque materials such as platinum or gold. The stent 18 may also be formed from a bioabsorbable material. Exemplary stents include the Evolution® controlled release stent and Esophageal Z-Stent (Cook Medical, Inc.).

The stent 18 may be bare, partially covered or fully covered with one or more graft materials. A stent used for placement in the gastrointestinal tract, for example, may be covered or encased on its inner or outer surfaces with silicone to prevent tumor or tissue ingrowth and decrease food bolus impaction, while the proximal and/or distal stent ends may be uncovered, and may include barbs or other structures to anchor the stent 18 within the body lumen and lessen the risk of migration. Other suitable graft materials may include polytetrafluoroethylene, Thoralon™ material, dacron, polyamide, small intestine submucosa, collagenous extracellular matrix and any other suitable material depending on the intended use or location of stent placement.

The inner catheter 22 and outer catheter 20 extend from a distal end of the delivery device to a proximal end of the delivery device. The proximal end of the device comprises an external manipulation section or handle 24, which is intended to remain outside of the patient during use. One example of a delivery device handle is described in U.S. Pat. Publication 2010/0168834 (Wilson-Cook Medical Inc., and Cook Ireland Limited) which is incorporated by reference herein in its entirety.

The inner catheter 22 remains fixated to the handle, such as at a rear hub 26, while the outer catheter 20 is axially moveable with respect to the inner catheter 22. For example, as shown in FIGS. 10 and 11, the outer catheter 20 may be affixed to a movable belt or other mechanism 52 such that actuation of a spring-loaded trigger 28 pulls the outer catheter 20 in the proximal direction relative to the inner catheter 22 to expose the self-expanding prosthesis 18. A directional switch 30 may be engaged to reverse the direction of the outer catheter 20 prior to actuating the trigger 28. An internal gear-pulley mechanism 54 enables the bidirectional movement of the outer catheter 20, such that the outer catheter 20 can be withdrawn proximally to expose the stent 18, or pushed distally to re-sheath the stent 18 to allow for repositioning. For example, a first gear set resheaths the outer catheter (i.e., moves the outer catheter in a distal direction relative to the inner catheter) and a second gear set retracts the outer catheter (i.e., moves the outer catheter in a proximal direction relative to the inner catheter). Further details of an internal gear-pulley mechanism in an exemplary handle are described in U.S. Pat. Publication 2010/0168834. It is also contemplated that other handles or external manipulation sections may be used with the delivery device 16 to facilitate movement of the outer catheter 20 relative to the inner catheter 22 to allow deployment of the stent 18 within a patient, including but not limited to a push-pull delivery system design or other suitable handle mechanisms as would be recognized as suitable by one of skill in the art.

As illustrated in FIGS. 5, 10 and 11, a steady sheath 32 extends over a portion of the outer catheter 20. A proximal end 34 of the steady sheath 32 may be secured to the distal end of the handle 24 by various means, including welding, adhesive, friction fit or other attachment mechanisms. Alternatively, the steady sheath 32 may be fixedly connected to the inner catheter 22. Irrespective of the manner of fixation, the steady sheath 32 is fixed against longitudinal movement relative to the inner catheter 22. In the embodiment illustrated, the steady sheath 32 is also fixed against longitudinal movement relative to the handle 24. The steady sheath 32 preferably includes a plurality of reference points 36 between its proximal 34 and distal 38 ends, which may include markings, numbers, bands, scales and other similar visible indicia 36 as illustrated in FIG. 6. The indicia 36 preferably have a known distance relationship to other portions of the delivery device 16. For example, the indicia 36 provided on the steady sheath 32 may correspond to a measured distance between the midpoint 14 of a stent 18 carried at the distal end of the delivery device 16 to a point near the proximal end 34 of the steady sheath 32, as indicated by arrow 40 in FIG. 5. In the particular embodiment illustrated in FIGS. 5 and 6, the indicia 36 provide the distance as measured in centimeters from the midpoint 14 of the prosthesis 18. In the embodiment illustrated, the distance between the midpoint 14 of the prosthesis 18 and the distal end of the steady sheath 32 is 14 centimeters. And since the first marking of the indicia 36 that is proximal of the distal end 38 of the steady sheath 32 is 1 centimeter, then the first marking of the indicia 36 indicates a distance of 15 centimeters. In other words, the distal-most marking of "15 cm" on the steady sheath 32 indicates that the distance from this marking to the midpoint 14 of the prosthesis is 15 centimeters. The indicia 36 therefore allow the user to determine the exact distance in centimeters between the midpoint 14 of the prosthesis 18 and any point along the steady sheath 32 without having to determine the distance between the prosthesis and the distal end 38 of the steady sheath. In other words, the indicia 36 can include distance markings that directly correspond to the distance to the midpoint 14 of the prosthesis 18. The indicia 36 could then be used to quickly and accurately position the delivery device 14 within the patient without the need for direct endoscopic visualization or fluoroscopy, so long as the location of the lesion has been previously determined (e.g., by determining the distance 40 of the lesion 4 from the patient's teeth 10).

Although the embodiment illustrated in FIG. 6 comprises indicia 36 indicting the distance (in centimeters) along the steady sheath 32 as measured from the midpoint 14 of the prosthesis 18, the indicia 36 could indicate the distance as measured from any other component of the delivery device 16, such as the distal end 38 of the steady sheath 32. Since the steady sheath 32 does not move relative to the inner catheter 22 or the prosthesis 18, the indicia 36 provide one or more reference points that may be used to verify that the delivery device 16 has not moved during deployment of the prosthesis 18. As will be explained in greater detail below, the indicia 36 on the steady sheath 32 can be used by the physician or assistant to determine the position of the prosthesis while the distal portion of the delivery device 16 is disposed within the patient, and more importantly, can be used to maintain that position during deployment of the prosthesis 18.

The steady sheath 32 is shown as extending distally from the distal end of the handle 24 and coaxially with the outer catheter 20, such that the steady sheath 32 covers a portion of the outer catheter 20. The steady sheath 32 may be linked, connected to or otherwise secured to the inner catheter 22 as shown in FIGS. 10 and 11. This may help stabilize the steady sheath 32 and inner catheter 22 and hold them in a stationary position with respect to each other. For example, the steady sheath 32 may be linked to the inner catheter 22 by a pin, rod, bridging structure or other attachment mechanism 42. Such an attachment mechanism 42 may extend through a portion of the outer catheter 20. As such, the outer catheter 20 may include one or more apertures, slots or channels 44 to accommodate an attachment mechanism 42 between the steady sheath 32 and inner catheter 22 that allows the outer catheter 20 to freely move axially while still permitting fixed attachment between the steady sheath 32 and inner catheter 22.

The steady sheath 32 may be of various lengths depending on the intended use, such that in one example it may extend substantially the full length of the outer catheter 20 and in another example it may only cover a short proximal portion of the outer catheter 20. However, the steady sheath 32 should not extend over the prosthesis 18 so as to not interfere with the deployment thereof. Preferably, the steady sheath 32 extends from the distal end of the handle and coaxially over the outer catheter 20 approximately ¼ to ⅓ of the length of the outer catheter 20, up to about ½ of the length of the outer catheter 20. Preferably, however, the steady sheath 32 extends distally from the distal end of the handle 24 and terminates at its distal end 38 in a location that would be in the back of a patient's throat when in use, as shown in FIGS. 5 and 10.

As best seen in FIGS. 5 and 7-9, the stent 18 is loaded onto the distal end of the delivery device 16 and held in a radially inwardly contracted delivery configuration by the outer catheter 20 (FIGS. 5 and 7) until the outer catheter 20 is withdrawn to expose the stent 18 (FIGS. 8 and 9). The distal tip 46 of the delivery device 16, the inner catheter 22 and the steady sheath 32 are "fixed" components that do not move relative to each other and/or the handle 24 during stent deployment. The outer catheter 20, however, is retracted proximally relative to both the inner catheter 22 and steady sheath 32 during deployment (or is advanced distally relative to the inner catheter 22 and steady sheath 32 during resheathing as will be described in further detail below). As such, the outer catheter 20 must axially move or slide in between the inner catheter 22 and the steady sheath 32. To facilitate ease of movement of the outer catheter 20 relative to these fixed components, a gap may be provided between the inner surface of the outer catheter 20 and the outer surface of the inner catheter 22. A gap may also be provided between the inner surface of the steady sheath 32 and the outer surface of the outer catheter 20. Preferably the gap(s) are small enough such that they do not unsuitably increase the diameter and/or size of the delivery device, but still allow for the outer catheter 20 to easily move axially during retraction and/or resheathing without the interference of excess frictional resistance with the inner catheter 22 or the steady sheath 32. The inner catheter 22, outer catheter 20 and/or the steady sheath 32 may also be coated or otherwise provided with a lubricous material to facilitate axial movement of the outer catheter 20. Alternatively, or in addition, a brace or reinforcing structure (not shown) may be provided between at least a portion of the steady sheath 32 and the outer catheter 20 to prevent collapse or compression of the steady sheath 32 upon the outer catheter 20. Likewise, if necessary or desired, a similar reinforcing structure may be provided between the outer catheter 20 and the inner catheter 22. In one non-limiting example, a cylindrical structure, tube and/or helical coil may be placed between the steady sheath and the outer catheter located distally of the distal end of the handle. Other suitable bracing structures are also contemplated that facilitate axial movement of the outer catheter 20 while serving to prevent the steady sheath 32 from compressing the outer catheter 20 (or prevent the outer catheter from compressing/collapsing upon the inner catheter 22) to lessen or eliminate any friction that may occur between the respective components when the physician manipulates the position of the outer catheter 20 relative to the inner catheter 22 and steady sheath 32.

In the embodiment illustrated, the steady sheath 32 has sufficient hoop strength to prevent collapsing thereof when being grasped by the physician or assistant. As will be explained below, it may be desirable for the physician (or assistant) to grasp the steady sheath 32 to prevent movement thereof (and the delivery device 14 in general) relative to the patient during deployment of the prosthesis 18.

As previously explained, a physician may use an endoscope 2 to determine the characteristics and location of an esophageal lesion 4 and identify the middle point 14 of the lesion 4 relative to another fixed point, such as the patient's teeth 10 as shown in FIGS. 1-4. This measurement may correspond to the indicia 36 on the steady sheath 32 to aid in the accurate positioning of the stent 18 relative to the lesion 4. Specifically, in one non-limiting example, if it is determined that the middle of a lesion 14 is 12 cm from the patients teeth 10 as measured by the endoscope 2 (or other suitable technology), the distal end of the delivery device 16 carrying the stent 18 is inserted into the esophagus until the 12 cm marking on the steady sheath 32 is aligned with the patients teeth 10 as shown in FIG. 5. This serves as an indication to the physician that a pre-selected or fixed point on the stent 18, such as the center 50 of the stent 18 carried on the distal end of the delivery device 16 is aligned with the center 14 of the lesion 4 as determined by measurement arrow 40 and shown in FIGS. 5 and 7.

Once the physician has determined that the stent 18 is accurately positioned at the desired location within the esophagus (or other bodily lumen), the outer catheter 20 can be proximally retracted to expose at least a portion of the stent 18 as shown in FIG. 8. Deployment of at least the distal portion of the stent 18 allows it to radially outwardly expand within the body lumen, until at least a portion of the stent 18 is anchored or implanted within the lumen by the radially outward expansive pressure alone or in combination with other anchoring structures of the stent 18 such as barbs (not shown). The stent 18 is preferably self-expandable, but alternatively, may be mechanically expandable by known methods such as balloon expansion and the like.

It is preferable that the physician hold the handle 24 steady and in a fixed position in space during stent deployment in order to keep the remainder of the delivery device 16 (and the stent being deployed) steady. Specifically, it is desirable to maintain the position of the inner catheter 22 and prosthesis 18 relative to the target lesion 4 of the patient during deployment of the prosthesis 18. As previously explained, maintain these components in a steady position can be difficult because the outer catheter 20 is moving relative to the inner catheter 22 and prosthesis 18 (as well as the target lesion 4 of the patient) during deployment. The steady sheath 32 provides indicia 36 visible to the physician to ensure that the handle 24, and more importantly the inner catheter 22 and prosthesis 18, are held in a fixed position relative to the patient's teeth 10 as stent deployment occurs, to eliminate or otherwise reduce the risk of misplacement of the stent 18 during deployment. The steady sheath 32 also provides a stable component of the delivery device 16 that may be grasped by the user (physician or assistant) at a location close to the patient (e.g., adjacent the patient's teeth 10) If it is determined that the stent deployment is occurring in the desired location, proximal retraction of the outer catheter 20 can continue to allow the remainder of the stent 18 to deploy within the body lumen as shown in FIGS. 5, 8 and 9.

At this stage of the procedure, and notwithstanding partial radial expansion of the stent 18, the delivery device may be activated to resheath the outer catheter 20 over the stent 18 to allow repositioning of the stent 18 within the esophagus. The physician may need to resheath and reposition the stent 18 as a result of having placed the stent 18 in the incorrect position. The resheathing feature gives the physician the ability to make real-time adjustments during the deployment procedure. The stent 18 may be able to be resheathed after about 10% of the stent has been deployed or up to as much as about 95% of the stent has been deployed. Preferably, the handle 24 includes a mechanism to reverse movement of the outer catheter 20 to a distal direction to facilitate resheathing. In one non-limiting example the directional switch 30 on the handle 24 may be pressed to actuate the gear-pulley system 54 within the handle 24, so that actuation of the trigger 28 enables the outer catheter 20 to move distally and resheath over the stent 18 until the stent is fully constrained back within the outer catheter 20. In order to prevent the stent 18 from moving as the outer catheter 20 moves distally during resheathing, a retaining element or anchor (not shown) may removably attach the stent 18 to the inner catheter 22. This helps to retain the stent in a substantially stationary position on the inner catheter 22 during the resheathing of the outer catheter 20 over the stent 18. Various types of stabilizing elements are contemplated, one example of which is shown and described in U.S. Pat. Publication 2010/0168834, which is incorporated by reference herein.

With the stent 18 fully recaptured within the outer catheter 20, the handle 24 and/or steady sheath 32 may be maneuvered to reposition the distal end of the delivery device 16 (carrying the stent 18) within the body lumen. After repositioning the stent 18 to a desired location, the directional switch 30 may be pushed to reactivate the gear-pulley system 54 such that proximal retraction of the outer catheter 20 again commences, thereby re-exposing the stent 18. After the stent has been satisfactorily repositioned and the outer catheter 20 retracted to allow stent deployment, any retaining element or mechanism and/or diameter reducing ties, if present, can be withdrawn or removed to finally release the stent 18 from the inner catheter 20, and the inner catheter withdrawn from the patient, leaving the stent 18 deployed in position within the patient as shown in FIG. 9.

The materials used to manufacture the components of the stent delivery device 16 described herein may be any materials known to one skilled in the art that are suitable for use in patients. By way of non-limiting example, the inner and outer catheter shafts 22, 20 and steady sheath 32 may be formed from polytetrafluorothylene (PTFE) particularly when a low friction sheath is desirable. Nylon and HDPE may also be used for clarity. Additional possible materials include, but are not limited to the following, polyethylene ether ketone (PEEK), fluorinated ethylene propylene (FEP), perfluoroalkoxy polymer resin (PFA), polyamide, polyurethane, high density or low density polyethylene, and nylon including multi-layer or single layer structures and the like and may also include reinforcement wires, braid wires, coils, coil springs and or filaments. The loops of any constraining members, retaining wires, sutures and/or diameter reducing ties may be made from common suture material as known in the art, for example polyester suture such as 4-0 Tevdek®, nylon, silk, polypropylene, ultra high molecular weight polyethylene (UHMPE), metallic alloy such as stainless steel or nickel titanium, bio-absorbable polymers and the like, and may be monofilament, braided, twisted or multi-filament.

One example of a delivery and deployment sequence of an esophageal stent using the disclosed delivery device 16 has been described above. However, it is contemplated that other implantable prostheses may also be used with the delivery device 16 for placement in other locations within a patient's body.

As explained above, the delivery device 16 comprises a proximal external manipulation section or handle 24 and a stent 18 carried on the distal end of the delivery device. The physician manipulates the delivery device 16 to track the distal end through the body lumen during the procedure and locate the prosthesis 18 at a desired deployment site within the esophagus. The handle 24 stays outside of the body during the procedure. In one example as shown in FIG. 5 and FIG. 10, the external manipulation section or handle 24 includes a trigger 28 and can be operated by the physician with a single hand to release the stent 18 into the body lumen. After having positioned the stent 18 in the target site within the esophagus, deployment of the stent 18 may begin.

The trigger 28 is actuated to enable proximal retraction of the outer catheter 20 relative to the inner catheter 22. In the handle embodiment shown in FIG. 5, the physician may grasp the trigger 28 of the device with a single hand, leaving the other hand free to perform other tasks. The trigger 28 is actuated multiple times to retract the outer catheter 20 in the proximal direction relative to the inner catheter 22 until a portion of the stent 18 has become exposed and partially radially expanded, as shown in FIG. 8. Further actuations of the trigger 28 cause the outer catheter 20 to proximally move back even further, thereby exposing an increasing portion of the self-expanding stent, as shown in FIG. 9.

In an alternative embodiment, other types of handles or external manipulation components may be used in connection with the delivery device 16. Specifically, other types of handles or manipulation components may be configured to perform or facilitate proximal retraction of the outer catheter 20 relative to the inner catheter 22 so as to deploy prosthesis 18. For example, the handle may comprise a first portion and a second portion, wherein the second portion is moveable relative to the first portion. The steady sheath 32 and/or the inner catheter 22 is fixedly connected to the first portion, and the outer catheter 20 is fixedly connected to the second portion. Movement of the second portion of the handle relative to the first portion of the handle causes movement of the outer sheath 20 relative to both the inner catheter 22 and the steady sheath 32.

In one example, the outer catheter 20 may comprise a transparent or translucent material (or a light-transmitting material) to enable the physician to visually observe the stent 18 and how it is positioned in relation to the esophageal lesion 4 and also be used as a visual indicator to determine how far the outer catheter 20 has been retracted and/or when resheathing capabilities have been lost. The outer catheter 20 can move proximally a predetermined threshold distance beyond which the physician will understand that the outer catheter 20 cannot be proximally retracted any further without losing the ability to resheath and recapture the stent 18 within the outer catheter. As proximal retraction of the outer catheter 20 continues, the stent 18 becomes uncovered and is allowed to fully radially expand within the body lumen as shown in FIG. 9. The entirety of the delivery device 16 may then be withdrawn from the patient, leaving the stent 18 deployed in place and completing the delivery sequence. For at least the reasons described herein, use of a steady sheath 32 placed outside of the outer catheter 20 aids in the accurate positioning and deployment of a stent 18 relative to a lesion 4 because the visible indicia on the steady sheath ensure that the delivery device 14 is held fixed in space relative to the patient (i.e, the. patient's teeth 10), thereby simplifying the procedure and increasing confidence by the user.

Throughout this specification, unless the context requires otherwise, the words "comprise" and "include" and variations such as "comprising" and "including" will be understood to imply the inclusion of an item or group of items, but not the exclusion of any other item or group items. While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but may reside in two or more of these combined together. Accordingly, the invention is not to be restricted.

The invention claimed is:

1. An assembly for delivering an endoluminal prosthesis to a patient, the assembly comprising:
    a proximal end and a distal end;
    an inner catheter extending between the proximal and distal ends;
    an endoluminal prosthesis releasably and circumferentially disposed about the distal end of the inner catheter;
    an outer catheter movably disposed about at least a portion of the prosthesis;
    a handle at the proximal end of the assembly, the handle operatively connected to the outer catheter and configured for imparting axial movement to the outer catheter relative to the inner catheter;
    a sheath fixed to at least one of the inner catheter and the handle, the sheath being disposed about at least a portion of the outer catheter and movable relative thereto, the sheath comprising a length that is sufficient to extend at least partially into the patient during delivery of the endoluminal prosthesis, the sheath comprising indicia visible to the user of the assembly, the indicia extending along a majority of the length of the sheath and being configured to identify a selected point on the sheath relative to the patient during delivery, the indicia identifying a particular measured distance from the selected point on the sheath to a selected point on one or more components of the delivery device;
    wherein the inner catheter and the sheath are separate fixed components that do not move relative to each other during axial movement of the outer catheter; and
    wherein the indicia is disposed along a portion of the sheath that is configured to extend into the patient during delivery of the endoluminal prosthesis, the indicia being configured to identify a particular measured distance from the patient to the selected point on one or more components of the delivery device.

2. The assembly of claim 1 wherein the handle comprises a first portion and a second portion, the second portion being moveable relative to the first portion, wherein the inner catheter is fixedly connected to the first portion of the handle and the outer catheter is fixedly connected to the second portion of the handle.

3. The assembly of claim 1 wherein the endoluminal prosthesis comprises a stent.

4. The assembly of claim 1 wherein the visible indica comprises at least one of markings, bands, scales and numbers.

5. The assembly of claim 1 wherein the visible indicia correspond to a measured distance between a selected point on the sheath and a selected point on the prosthesis.

6. The assembly of claim 5 wherein the prosthesis comprises a proximal end and a distal end and wherein the selected point on the prosthesis comprises a midpoint between the proximal and distal ends.

7. The assembly of claim 1 further comprising an attachment mechanism extending between the sheath and the inner catheter.

8. The assembly of claim 7 wherein the attachment mechanism comprises at least one of a pin, rod and bridge.

9. The assembly of claim 7 wherein the outer catheter comprises at least one aperture, slot or channel through which the attachment mechanism extends.

10. An assembly for delivering an endoluminal prosthesis to a patient, the assembly comprising:
- a proximal end and a distal end;
- an inner catheter extending between the proximal and distal ends;
- an endoluminal prosthesis releasably and circumferentially disposed about the distal end of the inner catheter;
- an outer catheter movably disposed about at least a portion of the prosthesis;
- a handle at the proximal end of the assembly, the handle operatively connected to the outer catheter and configured for imparting axial movement of the outer catheter relative to the inner catheter;
- a sheath affixed to the handle, the sheath being disposed about at least a portion of the outer catheter such that the outer catheter is movable relative thereto, the sheath comprising an overall length that is sufficient to extend at least partially into the patient during delivery of the endoluminal prosthesis, the sheath comprising indicia visible to the user of the assembly, the indicia being configured to identify a particular point on the sheath relative to the patient during delivery, the indicia identifying a particular measured distance from the particular point on the sheath to a selected point on one or more components of the delivery device;
- wherein the indicia is disposed along a majority of the overall length of the sheath and a portion of the sheath that is configured to extend into the patient during delivery of the endoluminal prosthesis, the indicia being configured to identify a particular measured distance from the patient to the selected point on the one or more components of the delivery device; and
- wherein the inner catheter and the sheath are separate fixed components that do not move relative to each other during axial movement of the outer catheter.

* * * * *